(12) United States Patent
Kim et al.

(10) Patent No.: US 8,236,320 B2
(45) Date of Patent: Aug. 7, 2012

(54) COMPOSITIONS AND METHODS FOR USING CA9 PROTEIN TO STIMULATE AN IMMUNE RESPONSE

(75) Inventors: Hyung L. Kim, Amherst, NY (US); Yanping Wang, Williamsville, NY (US); Xiang-Yang Wang, Williamsville, NY (US); John R. Subjeck, Williamsville, NY (US)

(73) Assignee: Health Research Inc., Buffalo, NY (US)

( * ) Notice: Subject to any disclaimer, the term of this patent is extended or adjusted under 35 U.S.C. 154(b) by 439 days.

(21) Appl. No.: 12/263,756

(22) Filed: Nov. 3, 2008

(65) Prior Publication Data

US 2009/0142365 A1    Jun. 4, 2009

Related U.S. Application Data

(60) Provisional application No. 61/001,602, filed on Nov. 2, 2007.

(51) Int. Cl.
*A61K 39/00* (2006.01)
*A61K 39/385* (2006.01)
*C12N 5/0784* (2010.01)

(52) U.S. Cl. .................................. 424/193.1; 424/277.1

(58) Field of Classification Search .................. None
See application file for complete search history.

(56) References Cited

U.S. PATENT DOCUMENTS

| | | | |
|---|---|---|---|
| 5,387,676 A * | 2/1995 | Zavada et al. | 536/23.5 |
| 6,027,887 A | 2/2000 | Zavada et al. | |
| 2005/0112134 A1 | 5/2005 | Graddis et al. | |
| 2008/0085285 A1 | 4/2008 | Kim et al. | |

FOREIGN PATENT DOCUMENTS

| WO | WO01/23421 | * | 4/2001 |
| WO | WO 03/100029 | * | 12/2003 |

OTHER PUBLICATIONS

Wang et al (Mol Cancer Ther, 2008, vol. 7, pp. 3867-3877).*
Pastorekova et al (Virology, 1992, vol. 187, pp. 620-626).*
Zavada et al (Arch. Virol., 1991, vol. 118, pp. 189-197).*

* cited by examiner

*Primary Examiner* — Karen Canella
(74) *Attorney, Agent, or Firm* — Hodgson Russ LLP

(57) ABSTRACT

Provided are methods for stimulating an immune response to an antigen by administering a composition to an individual in an amount effective to stimulate an immune response to the antigen. The stimulated immune response to the antigen is greater than the immune response stimulated by the antigen in the absence of CA9 protein. The compositions provided contain a complex that includes an antigen and an isolated CA9 protein.

11 Claims, 6 Drawing Sheets

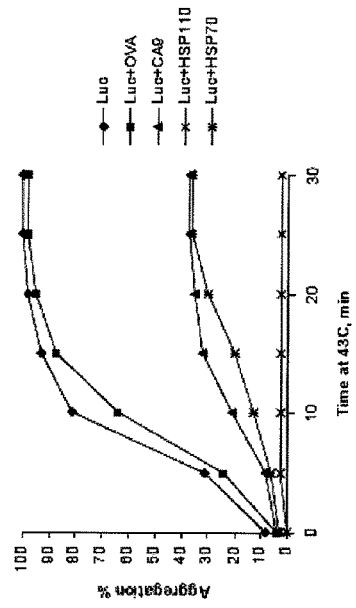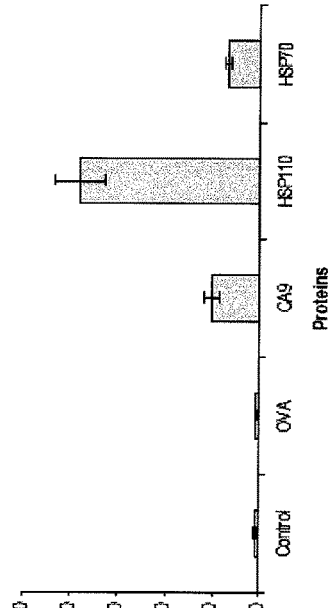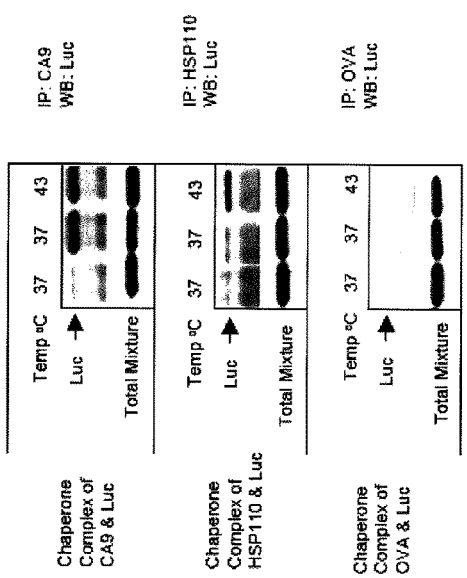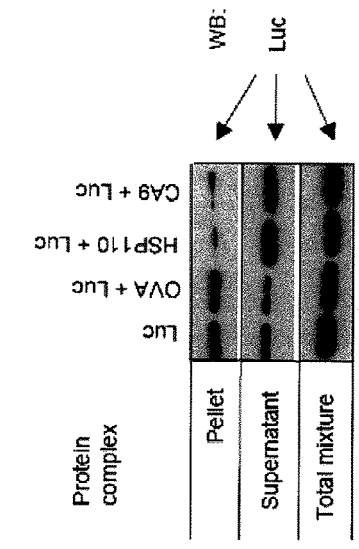
Figure 1A
Figure 1B
Figure 1C
Figure 1D

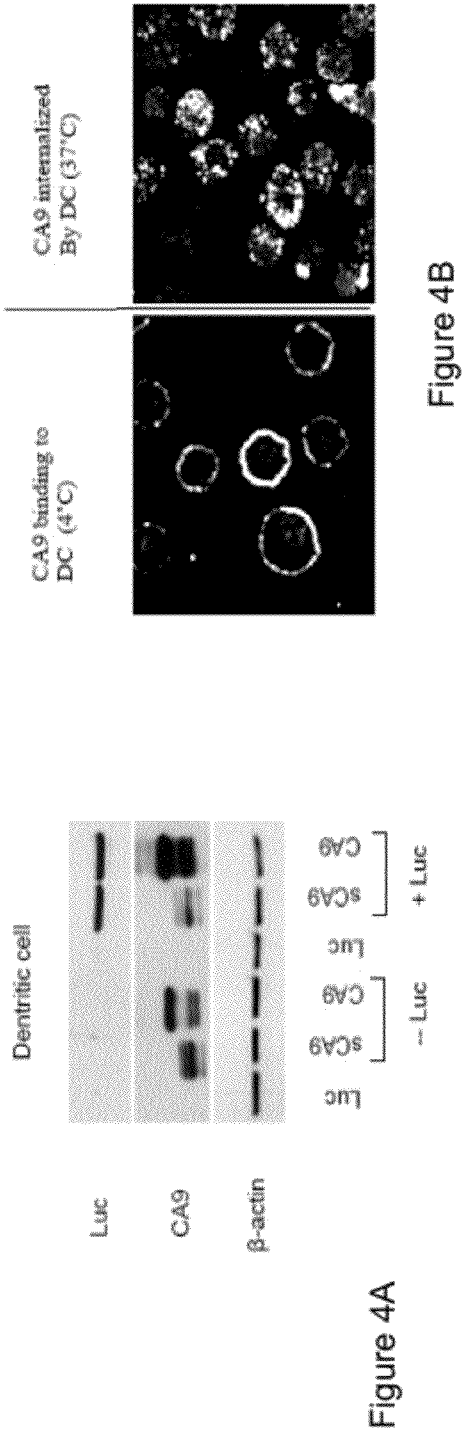
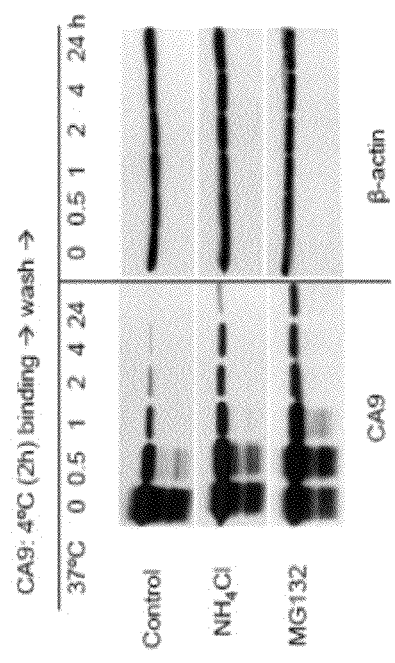
Figure 4A
Figure 4B
Figure 4C

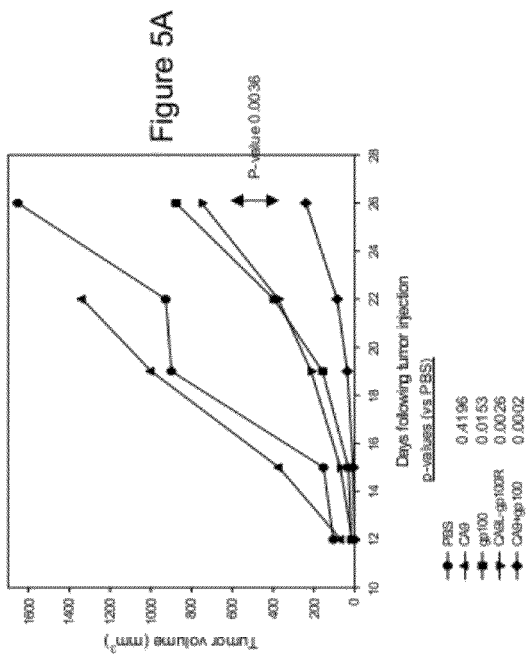
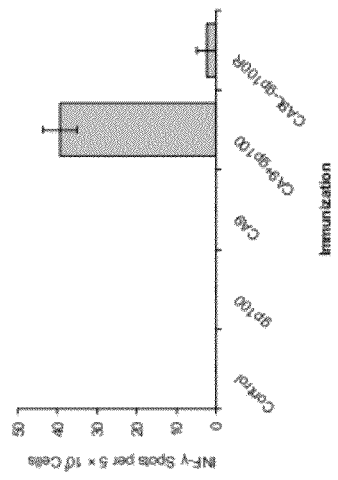
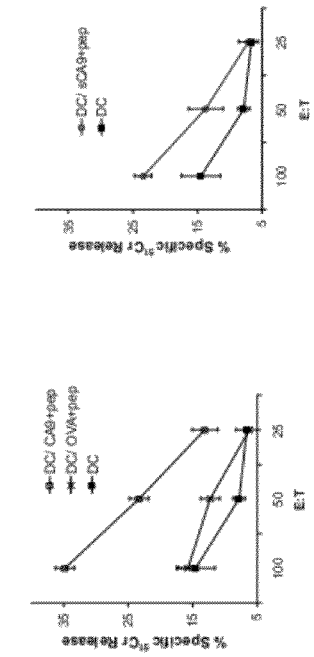
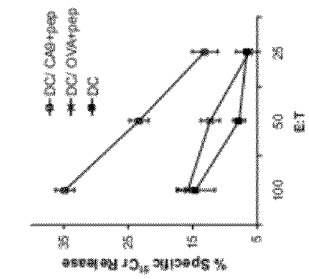
Figure 5A
Figure 5B
Figure 5C
Figure 5D

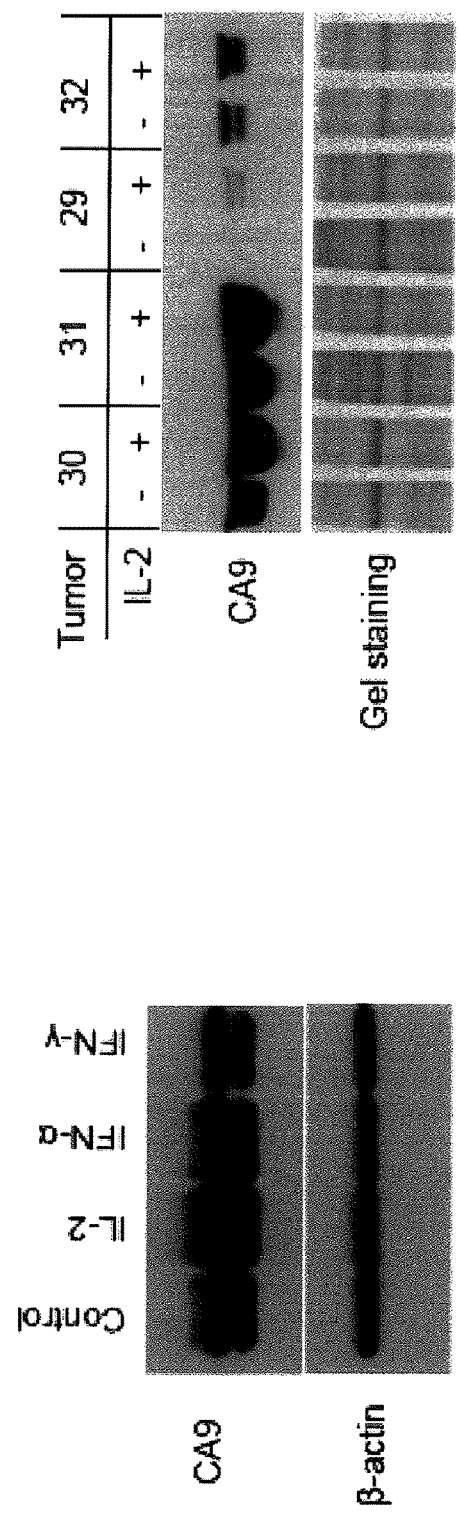

COMPOSITIONS AND METHODS FOR USING CA9 PROTEIN TO STIMULATE AN IMMUNE RESPONSE

This application claims priority to U.S. provisional application No. 61/001,602, filed on Nov. 2, 2007, the disclosure of which is incorporated herein by reference.

This work was supported by Grant No. 1K23CA12007501A1 from the National Institutes of Health. The Government has certain rights in the invention.

FIELD OF THE INVENTION

This invention relates generally to stimulating immune responses and specifically to the use of Carbonic anhydrase IX (CA9) as to stimulate an immune response against an antigen.

BACKGROUND

CA9 expression is associated with neoplastic growth and has been correlated with prognosis in cancers of the brain, lung, breast, cervix, kidney, gastrointestinal track, and head and neck (1-6). CA9 is expressed in response to decreases in oxygen tension (7). This is believed to be an adaptive response that results in increased delivery of oxygen and nutrients to the tumor and may favor disease progression and eventual metastasis of cancer cells. CA9 expression is increased in many solid malignancies, with greatest expression in tumor cells immediately adjacent to areas of necrosis (1, 7). CA9 is also a marker for hypoxia in normal cells and most malignancies. In all malignancies where CA9 has been reported as a prognostic biomarker, with the exception of clear cell renal cell carcinoma (RCC), increased CA9 expression predicted a worse prognosis (1-4, 6). Expression in other normal tissue is limited to basal cells of hair follicles, gonadal epithelium, choroid plexus, and some gastrointestinal mucosa (8). However, in clear cell RCC, CA9 expression is not regulated by oxygen tension. CA9 is present in over 80% of primary and metastatic RCC, and CA9 is present in 95-100% of the clear cell variant, the most common histologic type of RCC. CA9 is not expressed in normal renal tissue (8, 9). For clear cell RCC, CA9 appears to be an excellent biomarker that establishes diagnosis, determines prognosis, predicts treatment response, and serves as a target for therapy. In particular, high CA9 expression is an independent predictor of longer disease-specific survival in patients with metastatic RCC (5, 10), and improved survival in patients with localized RCC (11, 12). However, despite widespread interest in CA9 and better understanding of the molecular defect leading to CA9 overexpression in clear cell RCC, the mechanism linking CA9 expression to improved prognosis and treatment response in RCC patients, while being an indicator of an otherwise poor prognosis is not understood. Therefore, there is a need to develop methods and compositions employing CA9 for use as a therapeutic agent.

SUMMARY OF THE INVENTION

The present invention is based upon the surprising discovery of a heat shock protein (HSP) like chaperoning function for CA9. In particular, it is disclosed herein that CA9, as well as soluble form of CA9 that is shed from the surface of certain cells and is approximately 4 kDa smaller than full-length CA9, can inhibit heat-induced protein aggregation and can facilitate protein folding. However, unlike HSPs, we show that CA9 can form immunogenic complexes with antigens at room temperature (e.g., approximately 20° C.) and at human body temperature (e.g., 37° C.). CA9 is also shown herein to be internalized by antigen presenting cells and to be processed primarily through the proteosomal pathway, which is believed to be important for activation of cell-mediated immune responses. Further, we demonstrate in a murine melanoma model of cancer that the method of the invention is effective for stimulating an antigen-specific antitumor response that is greater than the response generated by the antigen in the absence of CA9 protein. Accordingly, the invention provides a method for stimulating an immune response to an antigen comprising administering a composition of the invention to an individual in an amount effective to stimulate an immune response to the antigen, wherein the immune response to the antigen is greater than the immune response stimulated by the antigen in the absence of CA9 protein. The compositions of the invention comprise an antigen and an isolated CA9 protein. The isolated CA9 protein and the antigen are provided in a complex, which complex may be a non-covalent association between isolated CA9 and the antigen, or may be a chemical conjugation of isolated CA9 protein to the antigen, or may be a CA9/antigen fusion protein. The immune response stimulated by administration of the composition may be prophylactic or therapeutic, and may comprise a humoral or cell mediated immune response, or combinations thereof. The invention is useful for stimulating an immune response against a wide variety of peptide and protein antigens, but heat shock proteins are not included within the scope of antigens used in the compositions and methods of the present invention. In one embodiment, the antigen is a tumor antigen.

BRIEF DESCRIPTION OF THE FIGURES

FIG. 1A provides a photographic representation of results from a pull-down assay used to show that CA9 is capable of binding client proteins. Luciferase (Luc) served as the client protein, and CA9 formed a complex with Luc at 37° C. and 43° C. HSP110 served as a positive control and formed a complex with luciferase at 43° C., but not at 37° C. Ovalbumin (OVA) served as a negative control and had no chaperoning ability. Lanes with no chaperone ($1^{st}$ lane) were included as controls. Immunoprecipitation (IP) was performed using antibodies against CA9, HSP110, or OVA followed by western blotting (WB) with anti-luciferase antibody. In the bottom panel, WB was performed with anti-luciferase to confirm that OVA pull-down was successful.

FIG. 1B provides a graphical representation of data demonstrating that recombinant CA9 is as effective as HSP70 in preventing aggregation of luciferase at 43° C. OVA served as a control protein. Luciferase aggregation was monitored over time by measuring optical density at 320 nm.

FIG. 1C is a photographic representation of Western blot analysis demonstrating that CA9 is able to prevent aggregation of luciferase and keep it in solution. Luciferase was heated to 43° C. for 30 min with or without chaperone protein (CA9, HSP10, OVA). The total reaction mixture was centrifuged at 16,000×g for 15 min to separate the supernatant and pellet. In the control reactions ($1^{st}$ 2 lanes), the majority of luciferase aggregated and was found in the pellet. CA9 and HSP110 were able to keep luciferase in solution at heat shock temperature. The total reaction mixture served as a loading control.

FIG. 1D provides a graphical representation of data demonstrating that isolated CA9 protein and classic heat shock proteins chaperone denatured proteins and allow refolding. Luciferase was denatured at 43° C. for 30 min in the presence of CA9, HSP110, HSP70, or OVA (negative control). Rabbit reticulocyte lysate (RRL) was added and refolding was assessed by monitoring the enzymatic activity of luciferase. The molar ratio of chaperone protein to luciferase was 20:1. Refolding ability correlated with ability to prevent aggregation of client proteins; CA9 and HSP70 were similar in its ability to prevent aggregation and refold luciferase. The mean±SEM is provided for experiments performed in triplicate.

FIG. 4A provides a graphical representation of data demonstrating that both CA9 and shed CA9 (sCA9) are able to bind and carry luciferase to DCs. CA9 and sCA9 were complexed to luciferase at 37° C. for 30 min and incubated with bone marrow derived DCs at 4° C. for 2 h. CA9 and sCA9 without luciferase, and luciferase alone were also incubated with DCs and served as controls. DCs were washed twice to remove unbound CA9, lysed in RIPA buffer, and probed by Western blot with anti-luciferase and anti-CA9 antibodies.

FIG. 4B provides a photographic representation of confocal microscopy analysis demonstrating that CA9 is capable of binding DCs and being internalized. Specifically, confocal microscopy showed FITC-labeled CA9 bound to the surface of bone-marrow derived DCs at 4° C. DCs were washed to remove unbound CA9 and incubated at 37° C. for 2 hours, resulting in internalization of FITC-labeled CA9. The nucleus was counterstained with DAPI.

FIG. 4C provides a photographic representation of Western blot analysis showing that DCs are able to internalize and process CA9. CA9 was allowed to bind DCs for 2 h at 4° C. DCs were washed twice and incubated in fresh medium at 37° C. for the indicated time. Cell surface CA9 was washed and intracellular CA9 was monitored by western blotting for CA9. β-actin served as a loading control. In the untreated (control) group, CA9 processing resulted in decreasing intracellular CA9 detected by western blotting. Pretreatment of DCs with MG132 (proteosome inhibitor) or $NH_4Cl$ (lysosome inhibitor) for 30 min at 37° C. indicated that CA9 was processed by both pathways; however, the proteosomal pathway was dominant.

FIG. 5A provides a graphical representation of results obtained from immunization of C57/BL6 mice (5 per group) with CA9-gp100 complex (CA9+gp100) which demonstrates stimulation of an antitumor effect against B16-gp100 tumor cells. B16-gp100 tumor cells ($2\times10^5$) were injected intradermally 7 days after 3 immunizations administered 7 days apart. Each line represents the mean tumor growth in five mice. P-values based on repeating measure ANOVA, which takes into account the variability within each group, are provided in the table comparing each group to the control mice injected with PBS. The rate of tumor growth was significantly different when comparing mice immunized with CA9+gp100 and mice in any control group; for example p-value was 0.0036 when comparing CA9+gp100 group and mice immunized with injection of CA9 and gp100 into separate flanks (CA9L-gp100R). Similar results were obtained in 3 separate experiments.

FIG. 5B provides a graphical representation of results obtained from immunization of mice with CA9+gp100, which stimulated a gp100-specific IFN-γ response from CD8+ cells measured using the ELISPOT assay. The mean±SEM is provided for experiments performed in triplicate.

FIG. 5C provides a graphical representation of results obtained from immunization of mice with CA9+gp100, which stimulated a tumor-specific cytotoxic T-cell response measured using the $^{51}Cr$ release assay. The mean±SEM is provided for experiments performed in triplicate.

FIG. 5D provides a graphical representations of results showing that shed CA9 is capable of stimulating a specific cellular immune response against murine gp100 peptide (EGSRNQDWL (SEQ ID NO:2)). Immunization with DCs treated with a complex of CA9 and gp100 peptide elicited a peptide-specific cytotoxic T-cell response measured using the $^{51}$Cr release assay. C57/BL6 mice (3 per group) were immunized 3 times, 7d apart, with 2×10$^6$ bone marrow-derived DCs treated with the indicated protein-peptide complexes at 10 μg/ml and activated with LPS. The mean±SEM is provided for experiments performed in triplicate.

FIG. 6A provides a photographic representation of Western blotting results obtained from an analysis of the effect of cytokines on CA9 shedding and expression. CA9 expression by the R6 RCC cell line was increased in response to media conditioned with human WBCs treated with IL2 and IFN-α. WBCs were separated from human blood and treated with IL2, IFN-α, IFN-γ, or nothing (control) for 24 hrs to produce conditioned media (CM). R6 cells were treated with CM for 48 hrs before lysing and probing with anti-CA9 antibody. CM was used since cytokines provide therapeutic benefit by stimulating immune cells rather than directly targeting tumors.

FIG. 6B provides a photographic representation of Western blotting results showing that CA9 shedding by primary tumor explants in short-term culture is increased in response to IL2. Primary renal tumors were cultured with or without IL2. The culture media were probed with anti-CA9 antibody. The culture media were resolved by electrophoresis and stained with coomassie blue to serve as a loading control. IL2 was applied directly to surgical specimens, which contain both tumor cells and immune cells.

DESCRIPTION OF THE INVENTION

Figure 2A:
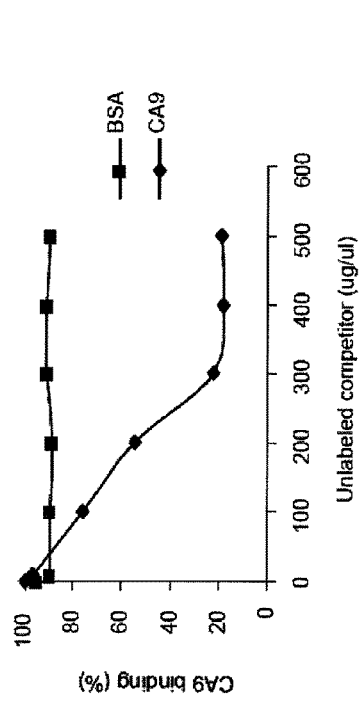
FIG. 2A provides a graphical representation of data showing that CA9 binds DCs in a saturable manner, which is indicative of receptor mediated binding. Bone marrow derived DCs ($1\times10^6$/ml) were incubated at 4° C. with FITC-labeled CA9 or FITC-labeled BSA for 30 min and washed twice with 1% BSA/PBS. CA9 binding was assessed by measuring the mean fluorescence intensity (MFI) using flow cytometry.

The present invention provides compositions and methods for stimulating an immune response to an antigen in an individual. The composition comprises a complex of isolated CA9 protein and an antigen. The method comprises administering the composition to an individual in an amount effective to stimulate an immune response to the antigen, wherein the stimulated immune response is greater than the immune response stimulated by the antigen alone. The stimulated immune response can have a therapeutic or prophylactic effect and can include a cell-mediated and/or humoral response, or a combination thereof.

The present invention is based upon the unexpected finding of a novel chaperoning function of CA9 and is believed to be the first discovery of a cell surface protein that can function as a chaperone. A "chaperone" is generally considered in the art to be a protein that can bind client proteins, prevent aggregation of the clients at heat shock temperatures, such as temperatures of approximately 42°-43° C., and allow refolding of denatured proteins. However, heat damage to proteins necessary for complexing with chaperone proteins can occur at temperatures up to approximately 55° C. Heat-shock proteins (HSPs) are well known, ubiquitous intracellular chaperones, the expression of which is driven by heat shock induced heat shock transcription factors, including HSF1, HSF2, HSF2BP, HSF4, HSF5, HSFX1, HSFX2, HSFY1 HSFY2. We demonstrate that CA9 possesses many functions conventionally attributed to heat shock proteins HSPs, and that a soluble form of CA9, which is shed from the surface of cells, also has HSP chaperoning properties. In particular, we demonstrate that CA9 inhibits heat-induced protein aggregation, enables refolding of denatured protein and restores enzymatic function to proteins with which it is complexed. We demonstrate that CA9 binds to dendritic cells (DCs) in a receptor-specific manner and show that bound CA9 is internalized by DCs and processed primarily through the proteosomal pathway, which is believed to be required for presentation of exogenous antigens on MHC I and activation of CD8+ T lymphocytes. Such antigen presentation is also believed to be important for a vaccine to stimulate an immune response that can inhibit the growth of tumors. Thus, these results collectively indicate that CA9 likely plays a direct role in stimulating an adaptive immune response. In this regard, we also demonstrate in a murine melanoma model of cancer that administering a composition comprising CA9 and an antigen can stimulate an antigen-specific antitumor response that is greater than the response generated by the antigen alone.

Notwithstanding the aforementioned similarities between CA9 and HSPs, CA9 has several unique and desirable features over HSPs, and is therefore not considered to be an HSP. For example, HSPs are induced by heat and, consistent with their role in providing thermal tolerance, HSPs bind target antigens at heat shock temperatures, e.g., 42°-43° C. In contrast, CA9 is induced not by heat (but by hypoxia), and we demonstrate that CA9 efficiently binds target antigens at 37° C. Moreover, CA9 can also form immunogenic complexes at room temperature. Thus, this property of CA9 may facilitate more efficient manufacturing of CA9-based compositions for use in the method of the invention. Additionally, HSPs are intracellular chaperones and are generally released to the extracellular environment only after cellular integrity has been disrupted. CA9, on the other hand, is a cell surface protein and also can be shed into the extracellular environment by viable cells. Furthermore, in cells with an intact hypoxia response, CA9 is expressed in response to decreases in oxygen tension. Therefore, and without intending to be bound by any particular theory, it is believed that the present invention reveals that CA9 expression and shedding may be a general mechanism for recruiting the immune system to target extracellular antigens in response to hypoxic stress, and may explain the favorable prognosis in RCC cases whereby soluble CA9 is shed from the tumors. Further, CA9 expressing cells in the host may represent a continuous source for production of an immune adjuvant that would serve to compliment the immunostimulatory effects of the present invention.

The amino acid sequence of full-length CA9 protein is:

```
  1    maplcpspwl pllipapapg ltvqlllsll llvpvhpqrl prmqedsplg ggssgeddpl (SEQ ID NO: 1)

61    geedipseed spreedppge edlpgeedlp geedlpevkp kseeegslkl edlptveapg 121    dpqepqnnah rdkegddqsh wryggdppwp rvspacagrf qspvdirpql aafcpalrpl 181    ellgfqlppl pelrlrnngh svqltlppgl emalgpgrey ralqlhlhwg aagrpgseht 241    veghrfpaei hvvhlstafa rvdealgrpg glavlaafle egpeensaye qllsrleeia
```

```
                                      -continued
301    eegsetqvpg  ldisallpsd  fsryfqyegs  lttppcaqgv  iwtvfnqtvm  lsakqlhtls 361    dtlwgpgdsr  lqlnfratqp  lngrvieasf  pagvdsspra  aepvqlnscl  aagdilalvf 421    gllfavtsva  flvqmrrqhr  rgtkggvsyr  paevaetga.
```

The human CA9 cDNA is known in the art and codes for a 459 amino acid protein with a 414 amino acid N-terminal extracellular part linked through a predicted 20 amino acid hydrophobic transmembrane region (TM) to a predicted 25 amino acid C-terminal intracellular tail (IC). The predicted sequence of the TM is provided in SEQ ID NO: 1 as amino acids 415-434. The predicted sequence of the IC is provided in SEQ ID NO:1 as amino acids 435-459. Thus, the predicted sequence of the shed CA9 protein is presented in SEQ ID NO:1 as amino acids 1-414.

The full-length CA9 has a predicted molecular weight of 49.7 kDa, but can be detected on Western blots as twin bands of 54 kDa and 58 kDa. The shed form of CA9 is a soluble form of CA9 that is released into the culture medium and into body fluids, most likely by proteolytic cleavage of the extracellular part from transmembrane and intracellular sequences. The shed CA9 is 4 kDa smaller than the full-length CA9 as detected on Western blots and thus migrates as twin bands of 50/54 kDa (Závada et al., Br J. Cancer. 2003 Sep. 15; 89(6): 1067-71), but has a predicted molecular weight of 45.7 kDa.

The compositions of the present invention comprise isolated CA9 protein. By "isolated CA9 protein" it is meant that the protein is separated from its natural environment. The CA9/antigen complexes described herein are considered to comprise isolated CA9 protein.

CA9 protein for use in the compositions and methods of the invention may be isolated from cells that express CA9 protein. Some non-limiting examples of such cells include cells that endogenously express CA9 protein from genomic coding sequences, and cells that have been engineered to express recombinant CA9 protein. Such recombinant expression of CA9 protein can be achieved using a wide variety of conventional techniques and recombinant protein expression systems known in the art. Alternatively, shed CA9 protein can be isolated using known methods from cell culture media in which cells that express CA9 via endogenous gene expression or genetic engineering are cultured. In the case of peptide antigens, the peptides may be chemically synthesized by any of a variety of well known techniques or may be obtained from proteolytic cleavage of larger proteins.

An isolated CA9 protein does not necessarily have to be a purified protein. However, isolated CA9 protein may nevertheless be purified to any desired degree of purification. Methods for protein purification are well known in the art and are applicable to obtaining purified CA9 protein for use in the present invention.

It is contemplated that the present invention can be used to stimulate an immune response to any protein, polypeptide or peptide antigen, with the exception that "antigen" and "antigens" as those terms are used herein do not include HSPs. Examples of HSPs include hsp40, calreticulin, hsp60, hsp70, hsp90, hsp110. Thus, except as otherwise described herein, antigens suitable for use in the present invention include but are not limited to antigens expressed by cancer cells or by infectious agents. The antigen may be well characterized, or may be unknown, other than by a known presence in, for example, a lysate from a particular cell type, such as a tumor or bacteria culture.

In one embodiment, the antigen present in the isolated CA9/antigen complexes of the invention is a tumor antigen.

Tumor antigens can be obtained by conventional techniques, such as by preparation of tumor cell lysates by repeatedly freezing and thawing tumor cells/tissues in phosphate buffered saline containing leupeptin and aprotinin (obtained from either fresh tumor biopsy tissues or from tumor cells generated in vitro by tissue culture). Such freezing and thawing results in lysis of cells. The tumor lysate can be obtained by centrifugation and harvesting the supernatant fluid. The tumor cell lysates can be used immediately or frozen and stored at, for example, −70° C. until ready for use.

In various embodiments, the antigen may be an antigen expressed by cancer cells, specific examples of which include but are not limited to fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, Waldenstrom's macroglobulinemia, and heavy chain disease. In one embodiment, the antigen is gp100.

In other embodiments, the antigens used in the invention may be those expressed by infections agents. Examples of such infectious agents include, but are not limited to viruses, bacteria, fungi and other parasites. Examples of viruses include, but are not limited to, hepatitis type B or type C, influenza, vaticella, adenovirus, herpes simplex virus type I or type II, rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus type I or type II. Examples of bacteria include, but are not limited to, M. tuberculosis, mycobacterium, mycoplasma, neisseria and legionella. Examples of other parasites include, but are not limited to, rickettsia and chlamydia.

Without intending to be bound by any particular theory, it is believed that for use in the method of the invention, the isolated CA9 protein and the antigen should be present in a complex, and thus are joined to each other by chemical bonding, such as by covalent bonds, ionic bonds, hydrogen bonds, and/or van der Waals bonds, or combinations thereof. Thus, in one embodiment, the CA9 protein and the antigen may be present in a complex wherein the CA9 protein and the antigen are not covalently bound to each other. Methods for forming protein/antigen complexes without covalent bonding are known in the art and can be employed to form complexes between isolated CA9 protein and one or more antigens. The complexes of the invention may comprise a CA9 protein and an antigen, or may consist essentially of a CA9 protein and an antigen, or may consist of a CA9 protein and an antigen.

In one embodiment, a complex comprising isolated CA9 and a non-covalently bound antigen can be formed in a suitable buffer at room temperature (e.g., approximately 20° C.), or at a higher temperature, such as 37° C., but below the higher temperatures typically required for HSPs to form a complex with a protein, such as 43° C. Accordingly, CA9/antigen complexes of the present invention may be formed at, for example, temperatures ranging from 20° C. to 42° C., inclusive, and including all integers between 20° C. to 42° C. The complexes may also be formed at higher temperatures. In one embodiment, the CA9/antigen complex is formed at 37° C. Suitable molar ratios of CA9 to antigen can be determined by those skilled in the art, given the benefit of the present disclosure. In one embodiment, a 1:1 molar ratio of CA9/antigen is used.

In one embodiment, for use in the present method, endogenous CA9 may be isolated from a biological sample comprising cells, such as a biological sample obtained from a tumor, and the isolated CA9 protein may thus be already complexed to tumor antigens against which an immune response is to be stimulated.

In another embodiment, the isolated CA9 protein can be covalently bound to the antigen, such as by chemically conjugating the CA9 protein to the antigen, to form a complex of isolated CA9 protein/antigen conjugate. Suitable methods for chemically conjugating proteins are known in the art and can be used to form isolated CA9 protein/antigen conjugates for the compositions and methods of the invention. Briefly, CA9 can be covalently conjugated to the antigen via crosslinking CA9 amino acid residues to antigen amino acid residues. The amino acid residues can be conjugated by, for example, crosslinking amino, sulfhydryl, or carboxylic acid groups using a wide variety of well known reagents and techniques.

In yet another embodiment, the CA9/antigen complex can be produced as a CA9/antigen fusion protein. Briefly, to produce such a fusion protein, DNA sequences encoding the CA9 protein and the antigen can be constructed using conventional techniques and expressed in a suitable cell type using any appropriate expression vector. The fusion protein can then be expressed in the cells and isolated using any method known to those skilled in the art. In one embodiment, the CA9/antigen fusion protein may be separated by a linker sequence.

In still another embodiment, isolated CA9 protein may be mixed with cellular material, such as a tumor lysate, to permit binding of CA9 with one or more tumor antigens present within the lysate, thereby forming a heterogeneous mixture of isolated CA9/antigen complexes that can be useful in the method of the invention as a multivalent cancer vaccine. Thus, it will be recognized that isolated CA9 proteins may be provided for use in the invention such that discreet isolated CA9 proteins are complexed with different antigens.

Any of a variety of delivery vehicles may be employed in the compositions and methods of the invention. Suitable delivery vehicles include but are not limited to antigen presenting cells (APCs), such as dendritic cells, macrophages, B cells, monocytes and other cells that may be engineered to be efficient APCs.

In one embodiment, the invention provides a composition and method for stimulating in an individual an immune response to an antigen comprising administering to the individual a composition comprising APCs, such as dendritic cells, which have been contacted with a complex comprising isolated CA9 protein and the antigen. The dendritic cells may comprise the CA9 protein/antigen complex at the time the dendritic cells are administered to the individual. This can be achieved by, for example, pre-loading the dendritic cells with the complex, or by transfecting the cells with DNA encoding the CA9 protein and the antigen as either distinct proteins or as a fusion protein.

When APCs are used, APCs, such as dendritic cells, may first be isolated from an individual and prepared for exposure to the CA9/antigen complex using conventional techniques. The dendritic cells may be isolated from the individual in whom a stimulated immune response to the antigen is desired, or may be isolated from a different individual.

In one embodiment, the invention provides a substantially purified population of dendritic cells that have been contacted with an isolated CA9/antigen complex.

For use in the compositions and methods of the invention, any suitable carrier known to those of ordinary skill in the art may be employed. The type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier may comprise water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. The compositions may also comprise buffers (e.g., neutral buffeted saline or phosphate buffered saline), carbohydrates (e.g., glucose, mannose, sucrose or dextrans), mannitol, antioxidants, chelating agents such as EDTA or glutathione, adjuvants (e.g., aluminum hydroxide) and/or preservatives.

The compositions of the invention can be administered using any suitable route of administration. Some non-limiting examples include oral, parenteral, subcutaneous, intraperitoneal, intrapulmonary, and intranasal. Parenteral infusions include intramuscular, intravenous, intraarterial, intraperitoneal, and subcutaneous administration.

Administration of the compositions of the invention can be performed in conjunction with conventional therapies that are intended to treat a disease or disorder associated with the antigen. For example, the composition could be administered prior to, concurrently, or subsequent to conventional anticancer therapies. Such therapies can include but are not limited to chemotherapies, surgical interventions, and radiation therapy.

In general, an appropriate dosage and treatment regimen provides the composition in an amount effective to stimulate an immune response that provides a therapeutic and/or prophylactic benefit. Such a response can be monitored by an improved clinical outcome, e.g., inhibition in tumor growth and/or metastasis, improved resistance to infection, improved immune cell activation, and/or other parameters that will be apparent to those skilled in the art, dependant upon the condition being treated.

Routes and frequency of administration of the therapeutic compositions disclosed herein, as well as dosage, will vary from individual to individual, and may be readily established using standard techniques. In general, the amount of each CA9/antigen present in a dose can range from about 100 μg to 5 mg per/kg of host. Suitable volumes will vary with the size of the patient, but will typically range from about 0.1 mL to about 5 mL. In one embodiment, a composition of the invention may be administered once weekly for a total of 3 doses.

EXAMPLE 1

This Example provides a description of the materials and methods that were employed in arriving at the invention.

Mice, Cell Lines and DNA Constructs

Female C57/BL6 mice, 6-8 week old, were purchased from NCI (Frederick, Md.) and housed under pathogen-free conditions. SR-A null mice were back-bred into the C57BL/6J background and were obtained from B. Berwin (Dartmouth University) as a generous gift of T. Kodama (Tokyo University) and M. W. Freeman (Massachusetts General Hospital, NHLBI Program in Genomics Applications). Human gp100 transduced B16 cells (B16-gp100) were kindly provided by Dr Alexander Rakhmilevich (University of Wisconsin, Madison, Wis.). R6, a human RCC cell line that expresses CA9, was a gift from Dr Arie Belldegrun (UCLA, Los Angeles). RENCA and RENCA cells stably transduced to express human CA9 (RENCA-CA9) were a gift from Dr Arie Belldegrun (UCLA, Los Angeles, Calif.). These cells were maintained in RPMI 1640, supplemented with 10% heat-inactivated fetal bovine serum (FBS; Life Technologies, Grand Island, N.Y.), 2 mmol/L of L-glutamine, 100 units/mL of penicillin, and 100 µg/mL of streptomycin.

The cDNA for mouse HSP110, mouse HSP70, human CA9, and human gp100 (a gift from Dr. Nicholas Restifo, National Cancer Institute, Bethesda, Md.) were cloned into pBacPAK-his vector (BD Biosciences Clontech, Palo Alto, Calif.), transformed into monolayer Sf21 cells using replication defective virus, and expressed using the BacPAK baculovirus system. Proteins were purified using a nickel nitriloacetic acid-agarose column (Qiagen, Valencia, Calif.). Protein concentrations were measured using a Protein Assay Kit (Bio-Rad, Hercules, Calif.). Protein purity was assessed using sodium dodecyl sulfate-polyacrylamide gel electrophoresis and Coomassie Blue staining. Endotoxin levels in recombinant proteins were assessed using a Limulus Amebocyte lysate kit (Biowhittaker, Walkersville, Md.) and were 10-25 endotoxin units/mg protein.

Formation of Chaperone-antigen Complex

To form a complex between chaperone (i.e. HSP110, CA9, OVA) and antigen (i.e. gp100 and luciferase), the 2 proteins were combined at 1:1 molar ratio and incubated for 30 min at 37° C. or at heat shock temperatures of 43° C. as previously described.(27) The complex was pre-treated with 30 µl protein G beads and immunoprecipitated using a mouse anti-human CA9 monoclonal antibody (a gift from Dr Egbert Oosterwijk, University of Nijmegen, Nijmegen, Netherlands), a previously described rabbit anti-hsp110 antibody (28), or mouse anti-OVA antibody (Sigma, St. Louis, Mo.). After SDS-PAGE (10%) electrophoresis, western blot analysis was performed using anti-luciferase (Promega, Madison, Wis.) or anti-gp100 antibody (Santa Cruz Biotechnology, Santa Cruz, Calif.).

Luciferase Aggregation and Refolding Assay

For the luciferase aggregation assay, 0.15 µM luciferase (Sigma, St Louis, Mo.) and chaperone protein (i.e. CA9, HSP110, HSP70) were incubated in 25 mM Hepes (pH 7.9), 5 mM magnesium acetate, 50 mM KCl, and 5 mM β-mercaptoethanol at 43° C. for 30 min. OVA served as a control for chaperone proteins. Protein aggregation was monitored by measuring optical density at 320 nm. To confirm that chaperone proteins were preventing aggregation, the solutions were centrifuged at 16,000×g for 15 min, and soluble and pellet fractions were separated, run on SDS-PAGE, and subjected to Western analysis with anti-luciferase antibody (Promega, Madison, Wis.).

For luciferase refolding assay, luciferase and chaperone protein were heated in refolding buffer (25 mM Hepes, pH 7.6, 5 mM $MgCl_2$, 2 mM dithiothreitol, and 2 mM ATP) at 43° C. for 30 min. The heated luciferase was diluted 100-fold into refolding buffer containing 60% rabbit reticulocyte lysate (Promega, Madison, Wis.) and incubated at 30° C. for 2 hr. To measure luciferase activity, the solution was further diluted 5-fold in 25 mM Hepes (pH 7.6), 1 mg/ml bovine serum albumin; 10 µl was added to 100 µl of luciferase assay solution (Promega, Madison, Wis.). Luciferase activity was quantified using a Lumat LB9501 luminometer (Berthoid, Bad. Wildbad, Germany).

Tumor Prevention and Immune Monitoring

Female C57/BL6 mice (NCI, Frederick, Md.), 6-8 week old (five per group), were immunized 3 times, 7 days apart, with 100 µl of vaccine. Mice were challenged with $2\times10^5$ B16-gp100 cells injected intradermally, 7 days after the last immunization. Tumors were measured every 3 days using an electronic caliper and tumor volume was calculated [(shortest $diameter^2\times$ longest diameter)/2]. The complete set of experiments was repeated 3 times. The ELISPOT and $^{51}$Cr Release assays have been described.(27) Briefly, lymph nodes (LNs) and spleen were harvested 2 wks after immunization. CD8+ T cells were isolated by negative selection using CD8+ cell-enrichment columns (Cedarlane Laboratories, Ontario, Canada). Enriched CD8+ T cells ($5\times10^4$/well) were incubated with DC 1.2 cells pre-pulsed with gp100 (10 µg/ml) at 37° C. for 48 h. IFN-γ spots were counted using the KS Elispot System (version 4.3.56) from Zeiss Microscopy (Oberkochen, Germany).

For the $^{51}$Cr Release Assay splenocytes and LN were harvested 2 wks after immunization and stimulated in vitro with mitomycin (50 µg/ml) pre-treated B16-gp100 cells for 5 d. Splenocytes were then serially diluted in 96-well plates containing $^{51}$Cr-labeled tumor cells ($1\times10^4$ cells/well) in triplicate with varying E:T ratios. After 8 h of incubation at 37° C., supernatant was analyzed for radioactivity using a gamma counter (Packard, Downers Grove, Ill.).

For the in vivo CTL assay, splenocytes were harvested from naïve mice to prepare target cells. Red blood cells were lysed and single-cell suspensions of splenocytes, $1\times10^7$ cells/ml, were pulsed for 30 min at 37° C. with or without 10 µM peptide in DMEM containing 10% FBS. The 2 cell populations at $2\times10^7$ cells/ml (in PBS/0.1% BSA) were labeled with different concentrations of CFSE (0.5 or 12.5 µM). CFSE labeling was stopped by adding an equal volume of FBS for 1 min and washing 3 times with RPMI 1640 complete medium. $5\times10^6$ cells each from the peptide-pulsed and unpulsed populations were mixed and injected i.v. into immunized and unimmunized mice.

Mice were sacrificed after 16 hrs. Single-cell suspensions of splenocytes were analyzed by flow cytometry. Percent specific lysis of fluorescent donor splenocytes in immunized mice was calculated as follows: [(number of unpulsed targets×A−number of pulsed targets)/number of unpulsed targets×A]×100, where A=[number of pulsed targets/number of unpulsed targets] in unimmunized recipient mice.

Generation of Immune Response with sCA9

Mice (five per group) were immunized 3 times, 7 days apart, with DC-based vaccines. The vaccination groups included DC treated with a complex of CA9 and murine gp100 peptide (EGSRNQDWL with >99% purity by HPLC, synthesized by Alpha Diagnostic international, San Antonio, Tex.) (CA9+pep), HSP110+pep, and sCA9+pep. Untreated DC and OVA+pep served as negative controls. To form protein-peptide complexes, 2 μg pep was incubated for 30 min with 20 μg proteins (OVA at 43° C., CA9 at 37° C., sCA9 at 37° C. or HSP110 at 43° C.). Peptide-protein complexes were added to bone marrow-derived DCs.

To generate DCs, marrows were harvested from murine femurs and tibias, and treated with red cell lysis buffer, washed and plated at a density of $1\times10^6$ cells per ml in 12-well plates in RPMI-1640 containing 10% FBS and 10 ng/ml of recombinant mouse granulocyte monocyte-colony stimulating factor (GM-CSF) (eBioscience, San Diego Calif.). Cells were fed every 2 days and harvested between days 7 and 9. Cultures consisted of 75-90% $CD11C^+$ cells. To generate vaccines, cultured cells were pulsed for 4-6 hours with 10 μg/ml protein-peptide complex and treated with 100 ng/ml LPS for 16 hours. $2\times10^6$ cells were injected subcutaneously into mouse. Seven days after the last immunization, lymph nodes and splenocytes were harvested for in vivo and in vitro CTL assays.

Response of CA9 to Cytokines

CA9 expression was monitored by probing R6 cell lysates with anti-CA9 antibodies after treating with conditioned media (CM) at 200 μl/ml for 48 hrs. WBCs were separated from whole blood obtained from healthy human subjects, and culture media from WBCs treated with 100 ng/ml cytokines or nothing (control) for 24 hrs served as the CM. To monitor CA9 shedding from short-term cultures of RCC explants, tumor fragments cut to 1 mm pieces (33 mg/ml) were rinsed with serum-free DMEM and cultured with or without IL2 (100 ng/ml) in DMEM with 10% FBS in 24 well plate and incubated at 37° C. in a 5% CO2 incubator for 3d. To quantify CA9 expression, tumor fragments were evaluated by Western blot using anti-CA9 antibody.

Binding of Chaperone-antigen Complex by Dendritic Cells (DCs)

To FITC-label CA9 or BSA (control protein), FITC (Sigma, St. Louis, Mo.) was added at 20 M excess in 0.1 M sodium bicarbonate/carbonate buffer. Free FITC was removed with a Sephadex G-25 column (Pharmacia, Piscataway, N.J.). Proteins were subjected to SDS-PAGE to confirm FITC conjugation.

To assess binding to DCs, FITC-conjugated proteins, 10 μg/ml, were incubated for 20 min on ice with murine bone marrow-derived DCs (see Generation of immune response with sCA9) at $1\times10^6$ cells/ml in 100 μL PBS containing 1% BSA. For the binding competition study, unlabeled CA9 or fucoidan was added at varying concentrations to $1\times10^6$ DCs/ml at 4° C. for 20 min. The DCs were washed 3 times with 1% BSA/PBS and then incubated with 200 μg/ml FITC-CA9. The nucleus was counterstained with DAPI.

The cells were fixed with 1% paraformaldehyde (Fisher, Fair Lawn, N.J.), and examined by confocal microscopy (Bio-Rad 600, Hercules, Calif.) and analyzed by flow cytometry (Becton Dickenson, La Jolla, Calif.).

Processing of Chaperone-antigen Complex by DCs

DCs were grown to 90% confluence, treated with 10 μM MG132 or 10 mM $NH_4CL$ for 2 h at 37° C. Untreated cells served as controls. Cells were cooled to 4° C. for 30 min before adding CA9 at 10 μg/ml. The cells were kept at 4° C. for an additional hour and then washed with cold RPMI 1640 complete medium. The cells were than warmed to 37° C., and harvest at 0, 0.5, 1, 2, 4, and 24 hr time points, washed and treated with radioimmune protection assay (RIPA) buffer (Sigma, St. Louis, Mo.) for 15 min on ice to lyse cells. 20 μg of lysate was subjected to Western blot analysis. The blots were probed with mouse anti-human CA9 antibody.

Short-term Kidney Tumor Culture from Surgical Specimens

Fresh human kidney tumors were obtained from the institutional tissue procurement service under an IRB-approved protocol (153605). Tumor tissues were cut to 1 mm pieces, rinsed with serum free RPMI 1640 medium, suspended in DMEM with 10% FBS and incubated in 100 mm Petri dishes at 37° C. in a 5% CO2 incubator. To quantify CA9 shed from tumors, the culture medium was harvested from a suspension culture after 2 days. To quantify CA9 levels in the tumor, small tumor fragments were treated with RIPA buffer. CA9 from the culture medium or cell extract were analyzed by Western blotting.

SCA9 was concentrated from RENCA-CA9 cells, which sheds a soluble form of CA9 that is 4 kDa smaller than CA9. RENCA-CA9 cells were cultured in 20 ml RPCI 1640 medium with 10% FBS. Cells grown to 100% confluence were cultured for an additional 24 hr in serum-free RPMI 1640. The culture medium was dialyzed for 24 hr with PBS and spun at 4000 rpm for 1 h in a concentrating tube. The concentration of sCA9 was measured by Western blot using purified CA9 as a standard. The medium from parental RENCA cells, which do not express CA9, was concentrated using the same protocol and served as a control.

Data Analysis

Error bars indicate+SEM for experiments performed in triplicate. Differences in tumor growth were assessed using repeating measure ANOVA. P-value<0.05 was considered statistically significant. Statistical analysis was performed using Stata 8.2 (StataCorp, College Station, Texas).

EXAMPLE 2

This Example describes the capability of isolated CA9 protein to act as a chaperone.

To evaluate CA9 for chaperoning function, luciferase was used as a reporter protein (FIG. 1A). HSP110, which is a heat shock protein with well characterized chaperoning function (29), served as a positive control and Ovalbumin (OVA) served as a negative control. CA9, HSP110, or OVA were mixed with luciferase at a 1:1 ratio. Immunoprecipitation was performed with antibodies against CA9, HSP110, or OVA and the complex was probed with antibodies to luciferase. HSP110 efficiently and irreversibility complexed luciferase at 43° C. CA9 was more efficient in complexing luciferase at RT than at 43° C.

To test whether formation of a complex between CA9 and luciferase protects luciferase from aggregation, CA9 and luciferase were mixed at 1:1 molar ratios and heated to 43° C. (FIG. 1B). Protein aggregation was monitored over time by optical densometry. HSP70 is another well characterized head shock protein. HSP110 and HSP70 were included as positive controls. HSP110 was able to completely prevent luciferase aggregation, and HSP70 and CA9 were equally effective in inhibiting luciferase aggregation. Ovalbumin (OVA) was a negative control and had no ability to prevent luciferase aggregation. In a confirmatory experiment, CA9 was able to keep luciferase in solution at 43° C. (FIG. 1C). A mixture of CA9 and luciferase was heated to 43° C. and centrifuged. Both CA9 and HSP110 were effective in keeping the majority of luciferase in the supernatant and out of the pellet.

HSPs assist with folding of newly synthesized proteins and refolding of denatured proteins. To assay for this function, a heat-denatured enzyme can be combined with chaperones in rabbit reticulocyte lysate and restoration of enzymatic activity can be monitored. To assess the ability of CA9 to refold denatured protein, luciferase was used as the reporter enzyme (FIG. 1D). HSP110 was the most effective chaperone for allowing heat-denatured luciferase to be refolded. CA9 and HSP70 were equally effective. OVA served as a negative control and did not facilitate refolding.

EXAMPLE 3

This Example demonstrates that isolated CA9 can bind to antigen presenting cells.

Figure 2B:
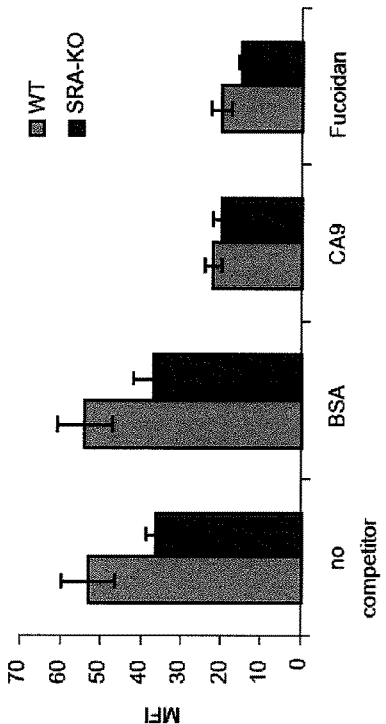
FIG. 2B provides a graphical representation of data showing a competition assay for CA9 DC binding. Binding of CA9 to DCs was inhibited by unlabeled CA9. Bone marrow derived DCs ($1\times10^6$/ml) were incubated at 4° C. with unlabeled CA9 or BSA at the indicated concentrations, washed, and then incubated with 200 μg/ml of FITC-labeled CA9.
Figure 2C:
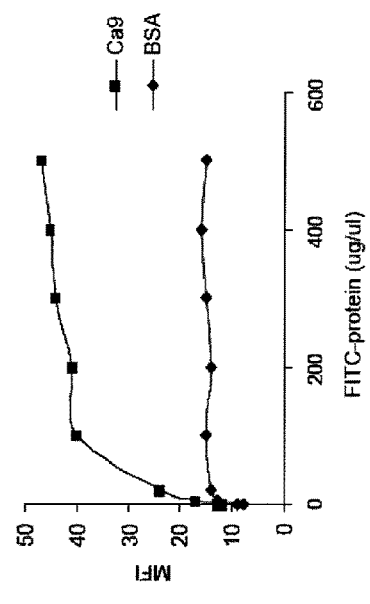
FIG. 2C provides a graphical representation of data showing that binding of CA9 to DCs is inhibited by scavenger receptor ligand. Bone marrow derived DCs ($1\times10^6$/ml) were incubated at 4° C. with fucoidan or BSA at the indicated concentrations, washed, and then incubated with 200 μg/ml of FITC-labeled CA9.
Figure 2D:
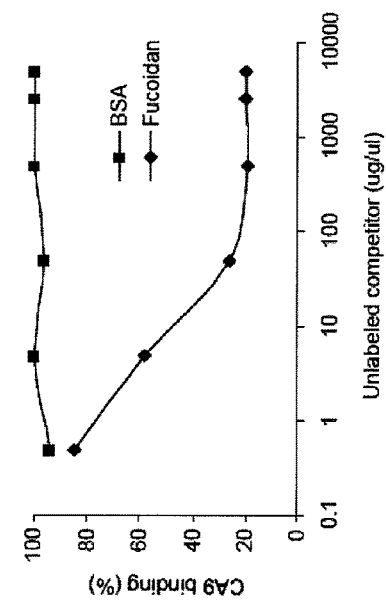
FIG. 2D provides a graphical representation of data showing that CA9 binding was decreased in DCs from scavenger receptor A (SRA) knockout mice (SRA-KO mice) when compared to DCs from wild-type mice (WT), indicating that CA9 binding is in part mediated by SRA. Bone marrow derived DCs ($1\times10^6$/ml) were incubated at 4° C. with BSA, CA9 or fucoidan at 500 μg/ml before being washed and then incubated with 200 μg/ml of FITC-labeled CA9. Error bars indicate SEM for experiments performed in triplicate.

We demonstrate that CA9 binds to DCs in a saturable manner, indicating receptor-specific binding (FIG. 2A). CA9 binding was blocked by unlabeled CA9 (FIG. 2B) and fucoidan (FIG. 2C), which is a ligand for scavenger receptors. Scavenger receptor A is one of many scavenger receptors on DCs. CA9 binding was decreased when the binding assay was performed using bone-marrow derived DCs harvested from scavenger receptor A knockout mice (FIG. 2D).

EXAMPLE 4

This Example demonstrates that shed CA9 acts as a chaperone.

Figure 3A:
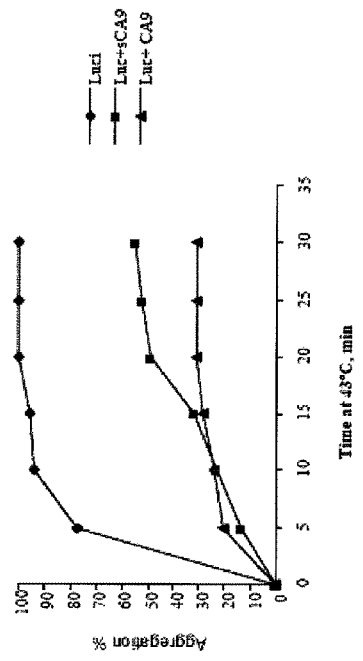
FIG. 3A provides a graphical representation of data demonstrating that tumor cells shed a soluble form of CA9. Cell lysates from human renal tumors were probed with anti-CA9 antibody, demonstrating expression of full-length CA9. The same tumors grown in short-term cultures shed a soluble form of CA9 (sCA9) that was approximately 4 kDa smaller in size than the full length CA9. Clear cell renal tumors (tumors 30-34) expressed and shed CA9. Normal kidney (Ki) and 2 papillary renal tumors (tumors 28 and 29) did not express or shed CA9.
Figure 3B:
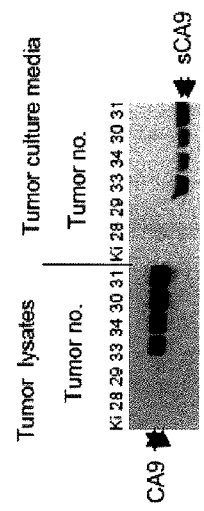
FIG. 3B provides a graphical representation of data demonstrating that shed CA9 has chaperone-like properties. SCA9 was as effective as full length CA9 in inhibiting the aggregation of luciferase at 43° C. Luciferase aggregation was monitored over time by measuring optical density at 320 nm.
Figure 3C:
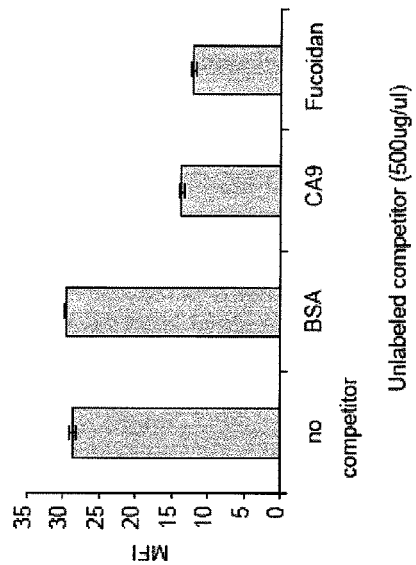
FIG. 3C provides a graphical representation of data showing that soluble CA9 binds DCs in a saturable manner. Bone marrow derived DCs ($1\times10^6$/ml) were incubated at 4° C. with FITC-labeled sCA9 or FITC-labeled BSA for 30 min and washed twice with 1% BSA/PBS (left). As with CA9, sCA9 binding to DCs was inhibited by unlabeled CA9 and fucoidan, suggesting that CA9 and sCA9 bind scavenger receptors on DCs (right). Bone marrow derived DCs ($1\times10^6$/ml) were incubated at 4° C. with BSA, CA9 or fucoidan at 500 μg/ml before being washed and incubated with 200 μg/ml of FITC-labeled CA9. Error bars indicate SEM for experiments performed in triplicate.
Figure 3D:
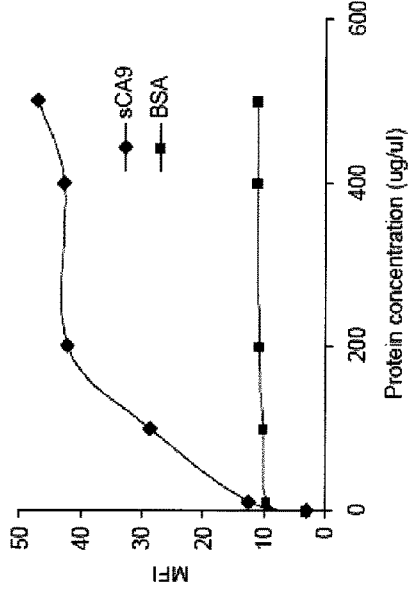
FIG. 3D provides a graphical representation of data establishing that soluble CA9 facilitates refolding of denatured protein. Luciferase was denatured at 43° C. for 30 min in the presence of CA9, sCA9, and HSP110. Rabbit reticulocyte lysate (RRL) was added, and refolding was assessed by monitoring the enzymatic activity of luciferase. The molar ratio of chaperone protein to luciferase was 20:1. CA9 and sCA9 were similar in its ability to refold luciferase. The mean+SEM is provided for experiments performed in triplicate.

Previous reports describe a soluble form of CA9 shed from the surface of RCCs.(25, 26) These reports were confirmed by blotting cell culture medium for CA9 (FIG. 3A). A soluble form of CA9 (sCA9), which was approximately 4 kDa smaller than the full-length CA9, was shed from a short-term culture of clear cell renal tumors. However, normal kidney and papillary renal tumors did not shed CA9. SCA9 and CA9 were equally effective in preventing the aggregation of luciferase at 43° C. (FIG. 3B). Key binding studies were repeated using sCA9 with results identical to those obtained for CA9. SCA9 also bound DCs in a saturable manner (FIG. 3C) and sCA9 binding was inhibited by unlabeled CA9 and fucoidan (FIG. 3D).

EXAMPLE 5

This Example illustrates CA9 mediated delivery of antigen to DCs and CA9 processing.

Delivery of antigens to DCs is an early step in generation of an adaptive immune response. Both CA9 and sCA9 were able to bind luciferase and deliver it to fresh murine DCs (FIG. 4A). A complex of sCA9 and luciferase was added to DCs at 4° C. Western blot analysis showed that luciferase bound to DCs when complexed to sCA9 or CA9, but not when luciferase alone was added to DCs. FITC-labeled CA9 bound to the surface of DCs at 4° C. as shown by confocal microscopy (FIG. 4B). When the cells were warmed to 37° C., labeled CA9 was internalized by DCs.

After internalization of CA9, the next step in activation of an adaptive immune response is processing of CA9 by DCs. Cell surface binding was monitored at 4° C. To monitor the status of internal CA9, cells were incubated at 37° C. to allow intracellular processes to occur. Cell surface CA9 was washed and intracellular CA9 was measured by probing the cell lysate. At 37° C., Intracellular CA9 rapidly increased, but was nearly undetectable within 4 hours (FIG. 4C). To evaluate the pathway for CA9 processing, intracellular CA9 levels were monitored in the presence of $NH_4Cl$ and MG132, which inhibit lysosomes and proteosomes, respectively. Although both $NH_4Cl$ and MG132 inhibited CA9 processing, MG132 was more effective in inhibiting CA9 processing. Therefore, intracellular CA9 is processed primarily by proteosomes, which process antigens for cross-presentation.

EXAMPLE 6

This Example demonstrates that administering a composition comprising a complex of isolated CA9 and an antigen stimulates an immune response to an antigen in vivo that is greater than the response stimulated by a composition comprising the antigen, but not comprising CA9.

To test whether CA9 can stimulate an antitumor immune response, a murine melanoma model was used to target a melanoma antigen, gp100. Recombinant CA9 and gp100 were complexed in vitro (CA9+gp100) and used to immunize C57/BL6 mice. The mice were challenged with syngeneic B16 tumors stably transduced with gp100. Mice immunized with CA9+gp100 had a significantly slower tumor growth (FIG. 5A) and longer survival when compared with any of the control groups (p<0.05, data not shown). Immunized with CA9+gp100 produced a gp100-specific IFN-γ response measured using the ELISPOT assay (FIG. 5B) and a tumor-specific cytotoxic T-cell response measured using the $^{51}Cr$ release assay (FIG. 5C). Therefore, immune monitoring demonstrated that CA9 is able to produce a gp100-specific cellular immune response.

Like full-length CA9, sCA9 was capable of stimulating a specific immune response. In the murine melanoma model described in FIG. 5A-C, human gp100 was used as the vaccine target. Therefore, gp100 itself produced a modest antitumor immune response; however, this model effectively demonstrates that gp100 immunity is augmented by CA9. In a confirmatory study, a murine gp100 peptide (pep) was evaluated as a target for generating a specific cytotoxic T-cell response. Mice were immunized with DCs treated with a complex of CA9 and pep (CA9+pep) or sCA9 and pep (sCA9+pep). Immunized mice developed pep-specific cytotoxic T-lymphocytes (CTL) as determined using the $^{51}Cr$ release assay (FIG. 5D).

EXAMPLE 7

This Example illustrates CA9 expression and shedding in response to cytokines.

CA9 expression in the primary renal tumor has been reported to predict response to IL2 therapy. As a screening study, CA9 expression was monitored in the human R6 RCC cell line after adding conditioned media (CM) from WBCs treated with various cytokines (FIG. 6A). CM was used since cytokines provide therapeutic benefit by stimulating immune cells rather than directly targeting tumors. CA9 expression increased in response to IL2 and INF-α, but not INF-γ.

Since CA9 has been reported to predict IL2 treatment response, we asked whether short-term culture of RCC explants increases CA9 shedding in response to IL2 (FIG. 6B). In all 3 clear cell RCCs examined, CA9 shedding increased in response to IL2. One papillary tumor with no baseline CA9 expression (tumor 29) shed low levels of CA9 after treatment with IL2. IL2 was applied directly to surgical specimens, which contain both tumor cells and immune cells.

EXAMPLE 8

This Example provides confirmatory evidence that CA9 is a prognostic marker in patients with renal cell carcinoma.

CA9 expression was quantified using real time, RT-PCR and frozen RCCs from 46 patients with clinically localized RCC who underwent surgical resection with curative intent. Table 1 summarizes the clinical and pathologic features. With a mean followup of 13.7 months, patients with low CA9 expression were significantly more likely to recur with metastatic disease (p=0.0326).

TABLE 1

Patient Characteristics

| | |
|---|---|
| Mean age (range) | 46 (43-88) |
| Male:Female | 22:24 |
| Stage (%) | |
| I | 26 (57) |
| II | 9 (20) |
| III | 11 (24) |

TABLE 1-continued

Patient Characteristics

| | |
|---|---|
| Fuhrman Nuclear Grade (%) | |
| 1 | 3 (7) |
| 2 | 26 (57) |
| 3 | 12 (26) |
| 4 | 5 (11) |

We claim:

1. A method for stimulating an immune response against an antigen in an individual, the method comprising administering to the individual a composition comprising a complex of isolated carbonic anhydrase IX (CA9) protein and an antigen, wherein the antigen is not a heat shock protein, wherein the administration of the composition stimulates an immune response against the antigen that is greater than an immune response stimulated by a composition comprising the antigen but not comprising the isolated CA9 protein.

2. The method of claim 1, wherein the complex is formed at a temperature between 30° C. and 42° C., inclusive.

3. The method of claim 1, wherein the complex is formed at 37° C.

4. The method of claim 1, wherein the antigen is a tumor antigen.

5. The method of claim 4, wherein the tumor antigen and the isolated CA9 protein are present in a complex formed by mixing the isolated CA9 protein with a tumor lysate.

6. The method of claim 1, wherein the composition further comprises antigen presenting cells that have been contacted with the complex prior to administration to the individual.

7. The method of claim 1, wherein the immune response against the antigen stimulated by administration of the complex comprises a cell-mediated immune response against the antigen.

8. A composition comprising a complex of isolated carbonic anhydrase IX (CA9) protein and an antigen, wherein the antigen is not a heat shock protein, wherein the composition is capable of stimulating an immune response against the antigen, wherein the stimulated immune response is greater than an immune response stimulated by a composition comprising the antigen without CA9 protein, and wherein the composition comprises a carrier suitable for use in administering the composition to an individual in need of the stimulated immune response.

9. The composition of claim 8, wherein the antigen is a tumor antigen.

10. The composition of claim 8, further comprising antigen presenting cells.

11. A composition comprising a substantially purified population of dendritic cells that have been contacted with the composition of claim 8.

* * * * *

SEQUENCE LISTING

<160> NUMBER OF SEQ ID NOS: 2

<210> SEQ ID NO 1
<211> LENGTH: 459
<212> TYPE: PRT
<213> ORGANISM: Human

<400> SEQUENCE: 1

```
Met Ala Pro Leu Cys Pro Ser Pro Trp Leu Pro Leu Ile Pro Ala
 1               5                  10                  15

Pro Ala Pro Gly Leu Thr Val Gln Leu Leu Ser Leu Leu Leu Leu
                20                  25                  30

Val Pro Val His Pro Gln Arg Leu Pro Arg Met Gln Glu Asp Ser Pro
                35                  40                  45

Leu Gly Gly Gly Ser Ser Gly Glu Asp Asp Pro Leu Gly Glu Glu Asp
    50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95

Glu Val Lys Pro Lys Ser Glu Glu Gly Ser Leu Lys Leu Glu Asp
                100                 105                 110

Leu Pro Thr Val Glu Ala Pro Gly Asp Pro Gln Glu Pro Gln Asn Asn
            115                 120                 125

Ala His Arg Asp Lys Glu Gly Asp Asp Gln Ser His Trp Arg Tyr Gly
    130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
            180                 185                 190

Leu Arg Leu Arg Asn Asn Gly His Ser Val Gln Leu Thr Leu Pro Pro
        195                 200                 205

Gly Leu Glu Met Ala Leu Gly Pro Gly Arg Glu Tyr Arg Ala Leu Gln
    210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

Thr Ala Phe Ala Arg Val Asp Glu Ala Leu Gly Arg Pro Gly Gly Leu
            260                 265                 270

Ala Val Leu Ala Ala Phe Leu Glu Glu Gly Pro Glu Glu Asn Ser Ala
        275                 280                 285
```

```
-continued

Tyr Glu Gln Leu Leu Ser Arg Leu Glu Glu Ile Ala Glu Glu Gly Ser
    290                 295                 300

Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
                325                 330                 335

Ala Gln Gly Val Ile Trp Thr Val Phe Asn Gln Thr Val Met Leu Ser
                340                 345                 350

Ala Lys Gln Leu His Thr Leu Ser Asp Thr Leu Trp Gly Pro Gly Asp
            355                 360                 365

Ser Arg Leu Gln Leu Asn Phe Arg Ala Thr Gln Pro Leu Asn Gly Arg
    370                 375                 380

Val Ile Glu Ala Ser Phe Pro Ala Gly Val Asp Ser Ser Pro Arg Ala
385                 390                 395                 400

Ala Glu Pro Val Gln Leu Asn Ser Cys Leu Ala Ala Gly Asp Ile Leu
                405                 410                 415

Ala Leu Val Phe Gly Leu Leu Phe Ala Val Thr Ser Val Ala Phe Leu
                420                 425                 430

Val Gln Met Arg Arg Gln His Arg Arg Gly Thr Lys Gly Gly Val Ser
            435                 440                 445

Tyr Arg Pro Ala Glu Val Ala Glu Thr Gly Ala
    450                 455

<210> SEQ ID NO 2
<211> LENGTH: 9
<212> TYPE: PRT
<213> ORGANISM: Mouse

<400> SEQUENCE: 2

Glu Gly Ser Arg Asn Gln Asp Trp Leu
1               5
```